United States Patent [19]

Pazell

[11] Patent Number: 5,071,410
[45] Date of Patent: Dec. 10, 1991

[54] ARTHROSCOPIC SURGERY SYSTEM

[76] Inventor: John A. Pazell, 6923 Belinder, Shawnee Mission, Kans. 66208

[21] Appl. No.: 669,648

[22] Filed: Mar. 14, 1991

[51] Int. Cl.$^5$ .......................................... A61M 29/00
[52] U.S. Cl. ................................... 604/164; 604/170; 606/191
[58] Field of Search ................. 604/165, 170; 606/191

[56] References Cited

U.S. PATENT DOCUMENTS

| | | | |
|---|---|---|---|
| 3,811,449 | 5/1974 | Gravlee | 604/191 |
| 4,306,562 | 12/1981 | Osborne | 604/164 |
| 4,417,886 | 11/1983 | Frankhouser | 604/170 |
| 4,449,532 | 5/1984 | Storz | 606/191 |
| 4,798,193 | 1/1989 | Giesy et al. | 604/164 |
| 4,981,482 | 1/1991 | Ichikawa | 606/191 |
| 4,994,027 | 2/1991 | Farrell | 604/164 |

OTHER PUBLICATIONS

Jul. 1989, Surgical Rounds for Orthopaedics, vol. 3, No. 7, A Complete System for Arthroscopy and Bursoscopy of the Shoulder; Stephen J. Snyder, M.D. pp. 57≅65.

*Primary Examiner*—Paul J. Hirsch
*Attorney, Agent, or Firm*—Hovey, Williams, Timmons & Collins

[57] ABSTRACT

An arthroscopic surgery system involves creating a passageway (18) in a predetermined location between the joint area (10) and the external surface (12) of the surrounding tissue (14) by inserting a pin (22), enlarging the passageway by passing a tubular rod (24) over the pin (22), and inserting a cannula (26) over the rod (24) to further enlarge the passageway (18) and to thereby allow insertion of surgical instruments (28) into the joint area. Use of this method avoids multiple punctures of tissue and joint capsule and reduces associated trauma and morbidity. Where the joint area is visualized through an arthroscope (20), the method permits precise triangulation at any angle to the arthroscope.

15 Claims, 2 Drawing Sheets

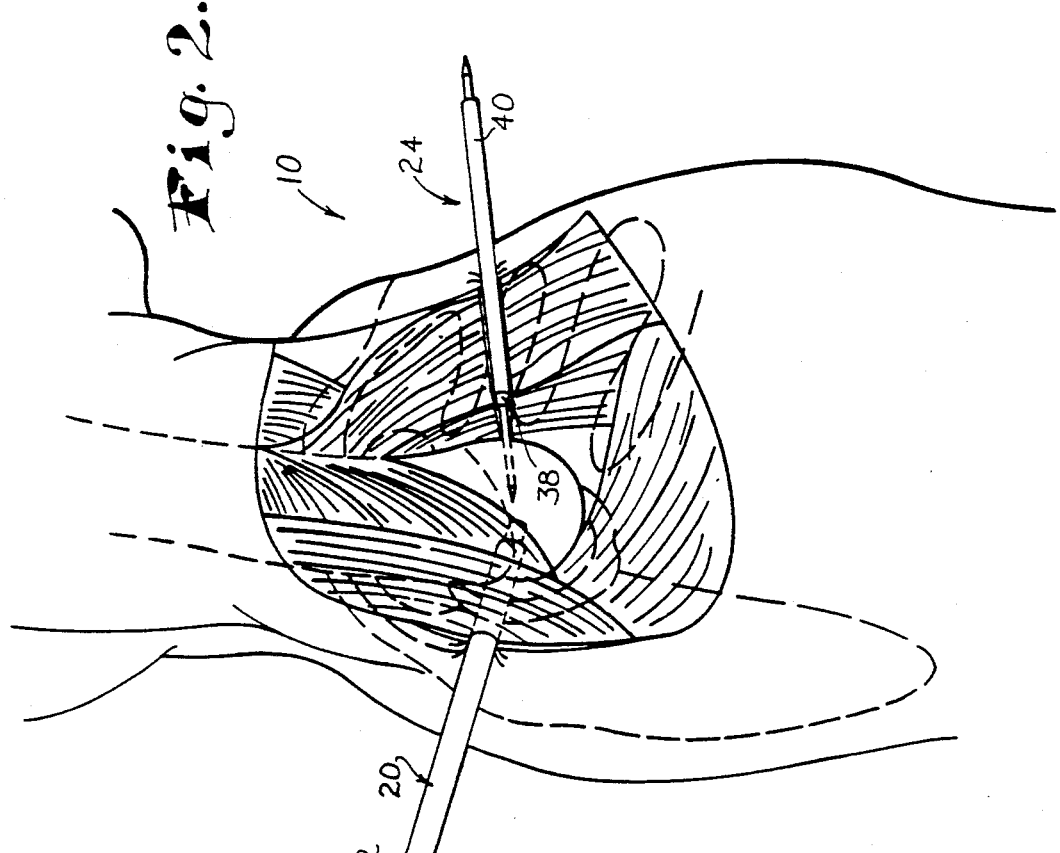
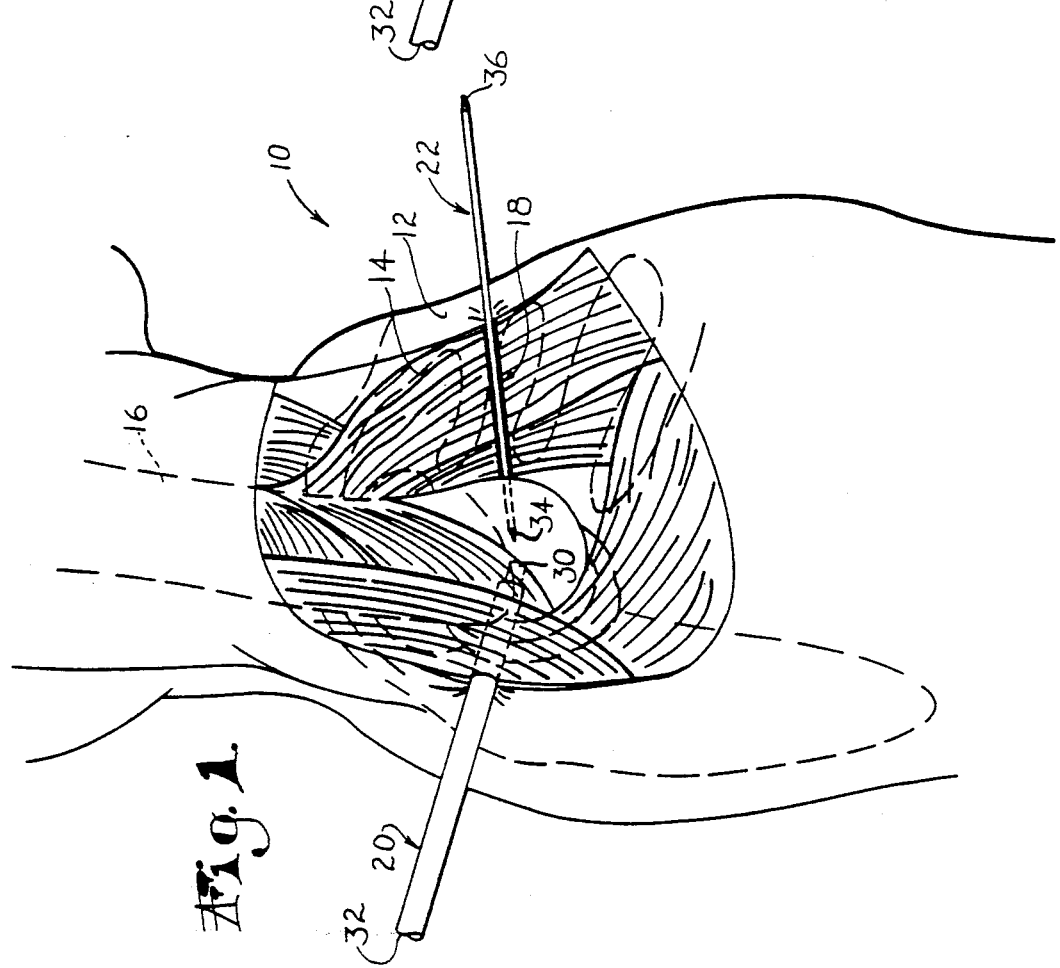

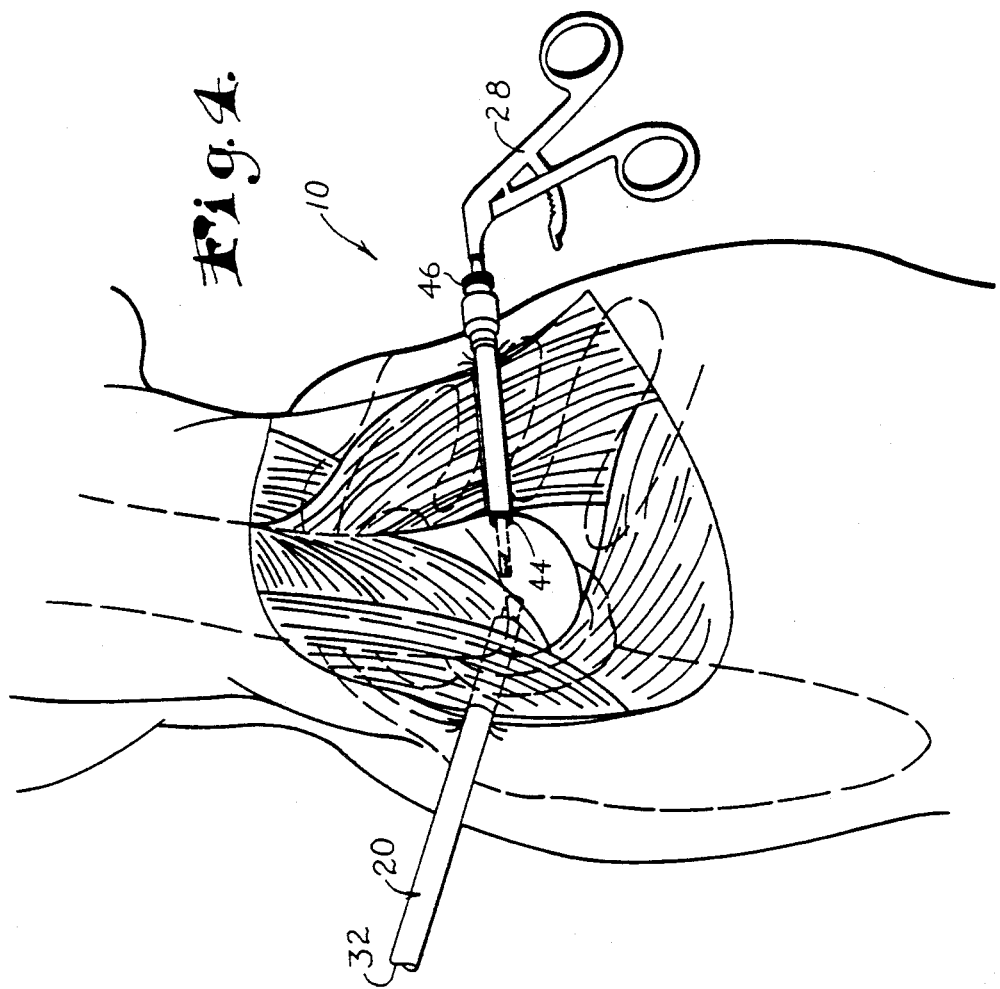
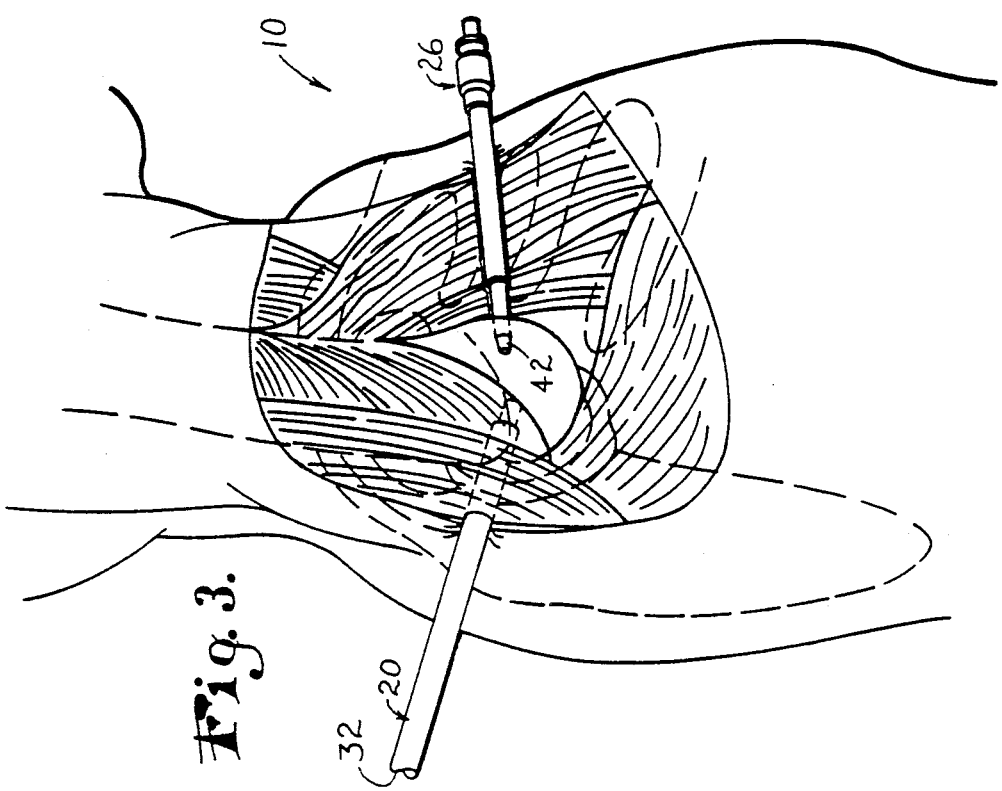

ARTHROSCOPIC SURGERY SYSTEM

BACKGROUND OF THE INVENTION

1. Field of the Invention

The present invention is broadly concerned with an improved method of performing surgery on a joint surrounded by tissue which permits accurate insertion of instruments into a predetermined location in the joint area with a minimum of trauma to the surrounding tissues. More particularly, it is concerned with a method in which a passageway is created in a predetermined location between the joint area and the external surface; the passageway is enlarged; and a cannula is inserted through which instruments are inserted into the joint area.

2. Description of the Prior Art

Arthroscopic examination of the interior surfaces of various joints and therapeutic procedures within the joints have become relatively commonplace methods of diagnosis and treatment in recent years. These techniques remain limited in their application, however, as to both the joints and patients which may qualify as candidates for such procedures. Healthy, young athletes with lax joints present the most suitable candidates. Patients with loss of motion or narrowing of the joint space are considered less than ideal candidates since introduction of instruments into the joint space is difficult.

A number of methods of performing arthroscopic surgery have been proposed in the past. In general, however, these methods are relatively slow, and have caused excessive trauma to the surrounding tissue resulting in postoperative morbidity, and extended immobilization and rehabilitation.

One such prior method, the spinal needle trial technique, typically involves insertion of a spinal needle from the posterior through layers of fat and muscle until it penetrates the joint capsule. Saline solution is injected for distension and, if the needle is correctly positioned into the joint capsule, saline will freely backflow from the needle. If there is no free backflow, the needle is removed and repositioned, further traumatizing the tissue.

Once correctly positioned, the needle is withdrawn, leaving a puncture wound, and an incision made through the skin at the needle insertion point. A sharp trocar in an arthroscope sleeve is then introduced into the incision and blindly directed along the path of the puncture wound anteriorly to enlarge the pathway and penetrate the capsule. With this technique, because of the small size of the wound left by the needle and the tendency of the surrounding tissue to close in, the trocar frequently deviates from the path of the original puncture, creating a second pathway, and penetrating the capsule at a different point. This results in further trauma to the tissue and multiple punctures through the joint capsule. In addition, the trocar and sleeve may be difficult to visualize through the arthroscope. If the deviation is substantial, it may be necessary to withdraw the trocar and sleeve and attempt another trial. Next, an arthroscope adapter is installed on the sleeve. The arthroscope may be used to visualize the joint area while the method is repeated to establish an alternative portal through which surgical instruments may be inserted.

An alternate procedure using a Wissinger rod may be used to establish an anterior portal. The rod is inserted through the arthroscope cannula into the joint area, and on through the anterior capsular tissue until it tents the anterior skin. Since the rod is inserted through the arthroscope cannula, the arthroscope itself is occluded and cannot be used for visualization of placement of the rod in the joint area. An incision is made in the skin in the area of the tip of the rod and a cannula is passed over the rod and into the joint area. The Wissinger rod is then withdrawn posteriorly.

The Wissinger technique presents some risks in that on certain joints neurovascular structures could be encountered. Additionally, the Wissinger technique is somewhat limited in its application. It is applicable only to joints such as the shoulder in which the rod can pass through the entire joint. In joints such as the knee where the Wissinger technique is inapplicable, the anterior portal must be triangulated by spinal needle trial. The cannula through which the rod is to be inserted must be carefully positioned because its angle of entry predetermines the exit path of the rod. A small variance in the angle of entry necessarily results in a substantial deflection of the exit point. Improper orientation of the rod may result in injury to underlying neurovascular structures.

Where additional portals are required for examination or therapeutic purposes, they must be developed by the spinal trial technique because placement of the rod cannot deviate from the angle predetermined by the angle of placement of the arthroscope.

SUMMARY OF THE INVENTION

The present invention overcomes the problems outlined above and provides a greatly improved method for performing arthroscopic surgery on a joint surrounded by tissue. Use of the method of the invention decreases the number of punctures to the capsule of the joint or cavity to which the instrument is inserted, reduces the time required in surgery, and results in a concomitant decrease in trauma and morbidity. Additionally, the prescribed technique is applicable to virtually all joints and any endoscopic technique.

The method in accordance with the present invention involves creating a passageway between the joint area and the surrounding tissue to the surface of the skin, enlarging the passageway by passing a tubular rod over the pin, and inserting a cannula over the rod to further enlarge the passageway, removing the pin and the rod from the passageway, and inserting surgical instruments through the cannula and into the joint area. Remote visualization of the joint area using an arthroscope has been found to be particularly useful.

BRIEF DESCRIPTION OF THE DRAWINGS

FIG. 1 is a side elevation of a human shoulder joint with a portion of the joint broken away to expose an arthroscope and pin in place as used in the method of the invention.

FIG. 2 is a side elevation of a human shoulder joint with a portion of the joint broken away to expose an arthroscope, pin and rod in place.

FIG. 3 is a side elevation of a human shoulder joint with a portion of the joint broken away to expose an arthroscope, rod and cannula in place.

FIG. 4 is a side elevation of a human shoulder joint with a portion of the joint broken away to expose an arthroscope, cannula and surgical instrument in place.

DESCRIPTION OF THE PREFERRED EMBODIMENT

Referring now to the drawings, a human shoulder joint area 10, which is the functional region of an arthroscopic surgical procedure, is shown in approximate lateral decubitus position. Certain parts of the shoulder joint include the skin 12, tissue 14, and humerus 16. A passageway 18 is created between the skin 12 and the surface of the bone 16. It is understood that the tissue as shown includes fat, joint capsular tissue, other bones, ligaments, tendons, blood vessels, nerves, fascia, and other anatomical structures.

The instruments employed in accordance with the method of the invention include an arthroscope 20, pin 22, rod 24, cannula 26, and forceps 28.

The arthroscope 20 has an insertion end 30 and a viewing end 32. Pin 22 includes opposed ends 34 and 36. Rod 24 includes an insertion end 38 and graspable end 40. A bevel 42 bridges the distance between the inner rod diameter and its outer diameter. Cannula 26 includes insertion end 44 and opposed end 46.

The inner diameter of rod 24 is such that it fits coaxially over pin 22. Likewise, the inner diameter of cannula 26 is such that it fits coaxially over rod 24. For example, the preferred outer diameter of the pin is about 0.030-0.065 inches, which is slightly smaller than the preferred inner diameter of the rod, about 0.110 inches. The preferred outer diameter of the rod in turn is about 0.170 inches, and about 0.140 inches at its tapered end which is slightly smaller than the preferred inner diameter of the cannula, about 0.11-0.190 inches, about 0.173 inches in particularly preferred forms. The outer diameter of the cannula is about 0.120-0.205 inches preferably about 0.203 inches. These dimensions permit smooth coaxial placement of the rod over the pin and the cannula over the rod. The thickness of the rod, at least about 0.05-0.075 inches, about 0.06 inches in preferred forms, serves to enlarge the passageway to accommodate the cannula. A bevel conjoins the inner and outer diameters of the rod with an acute angle in preferred forms which serves to enlarge the passage without trauma to the surrounding tissue.

As illustrated in FIG. 1, a human patient is positioned in the lateral decubitus position with the arm supported in approximately 70° abduction and 15°-20° forward flexion. One end 34 of a smooth surgical pin 22, such as a Steinmann pin, is inserted from the anterior through tissue 14 to create a passageway 18 into joint area 10. Those skilled in the art will appreciate that a spinal needle, preferably 18-gauge, may be used instead of a pin. In preferred embodiments, the joint area is remotely visualized using an arthroscope 32, which has been inserted through a posterosuperior portal. Placement of the pin is visualized and the surgeon is able to view placement of the rod over the pin. This technique permits the surgeon to quickly and precisely triangulate at any angle to the arthroscope without the need for repeated trials.

Any of the five portals commonly used in shoulder arthroscopy, or any other portal, may be used for placement of the arthroscope 32 or of pin 22, rod 24, and cannula 26. If a needle is used, once the shoulder is entered, the joint may be distended with saline solution to enhance remote visualization and enlarge the surgical field.

As shown in FIG. 2, the insertion end 38 of rod 24 is next placed over the pin and, following the same pathway as the pin, penetrates the joint capsule at the same point as the pin. The inner diameter of rod 24 is such that it will fit coaxially over pin 22, without leaving a large gap which might serve to traumatize the tissue as the rod is inserted. The outer diameter of rod 24 is substantially larger than the inner diameter, and the two are joined by a bevel 42, to facilitate insertion of the rod through the tissue. It is necessary for the rod to be of sufficient thickness to provide a transition between the relatively narrow diameter of the pin or needle and the inner diameter of cannula 26, which must be adequate to allow for the passage of surgical instruments. Once the rod 24 is placed in the joint area, the pin 22 may, but need not necessarily, be removed.

FIG. 3 illustrates the placement of cannula 26 over rod 24 in close coaxial relationship. At this point in the procedure the rod and, if still in place, the pin are removed to permit introduction of surgical instruments through the interior of the cannula as shown in FIG. 4.

While the method of the invention is applied herein to the shoulder joint as an illustration, it should be understood that the method is applicable to all other encapsulated joints and articulations, including but not limited to the hip, knee, elbow, wrist, and ankle. The method of the invention may also be applied to arthroscopic lumbar diskectomy. For such applications, the rod and cannula can be fabricated in any number of diameters and lengths. Smaller sizes, for example, would function in joints such as the wrist, finger or temporomandibular.

In addition, the method of the invention may be applied to endoscopic surgery of hollow organs including but not limited to such organs as the urinary bladder, gall bladder, and fallopian tubes. In such instances, an endoscope would be employed in place of the arthroscope. Larger sizes of the rod and cannula would be employed in great cavities such as the abdominal cavity, while smaller sizes would be employed in cavities such as the gallbladder.

In other embodiments, remote visualization could be accomplished in any number of other ways, as for example by sonogram, computerized tomography, or X-ray. The rod, cannula and other instruments of the invention may be constructed of any of a number of metals, synthetic resins or other suitable materials which can withstand sterilization. Where X-ray visualization is employed, they are preferably constructed of radio-opaque materials such as stainless steel.

While basket forceps are illustrated herein, a wide variety of surgical instruments can be inserted through the cannula into the area, such as scissors, grabbers, suction devices, and including electrosurgical motorized instruments, such as for shaving, abrading.

Having described the preferred embodiments of the present invention, the following is claimed as new and desired to be secured by Letters Patent:

1. A method of performing surgery on an area surrounded by tissue, said method comprising the steps of:
   creating a passageway between the area and the external surface of the surrounding tissue thereof by inserting a pin from said external surface through said surrounding tissue and thence into said area, such being the extent of the farthest penetration of said pin;
   enlarging said passageway by passing a tubularly shaped rod coaxially over said pin and through said passageway while maintaining said pin in place and while using said pin as a guide for said rod during insertion into said passageway;

inserting a cannula coaxially over said rod in order to further enlarge said passageway, said cannula presenting an inside diameter sufficient to allow insertion of instruments therethrough and into said area; and removing said pin from said passageway subsequent to insertion of said rod therein and removing said rod from said passageway subsequent to insertion of said cannula therein for allowing inserting of instruments through said cannula into said area.

2. The method set forth in claim 1, said method further including the step of providing remote visualization of said area.

3. The method set forth in claim 2, wherein said surgery is performed on a joint area and wherein said visualization step includes the step of using an instrument such as an arthroscope.

4. The method set forth in claim 2, wherein said surgery is performed on a body cavity and wherein said visualization step includes the step of using an instrument such as an endoscope.

5. The method set forth in claim 1, said tissue surrounding said area including skin presenting said external surface and, wherein said step of creating a passageway includes the step of inserting said pin first through said skin and thence into said area.

6. The method set forth in claim 1, wherein said cannula presents an inside diameter slightly greater than the outside diameter of said rod.

7. The method set forth in claim 1, said instruments inserted through said cannula into said area including arthroscopic surgical instruments.

8. The method set forth in claim 7, said arthroscopic surgical instruments including at least one of instruments for tissue shaving, electrosurgical instruments, and abrasion tools.

9. The method set forth in claim 1, wherein said removing step includes removing said pin after insertion of said rod and prior to insertion of said cannula.

10. A method of performing surgery on an area of the body surrounded by tissue including skin presenting an external surface, said method comprising the steps of:
    inserting a device into the area for providing remote visualization thereof;
    creating a passageway between the area and the external surface of the surrounding tissue thereof by inserting a pin first through said skin, then through said surrounding tissue, and thence into said area, such being the extent of the farthest penetration of said pin;
    visualizing said pin in said area through said remote visualization device;
    enlarging said passageway by passing a tubular shaped rod coaxially over said pin and through said passageway while maintaining said pin in place and using said pin as a guide for said rod during insertion into said passageway,
    said rod presenting an inside diameter slightly greater than that of said pin, presenting an enlarged outside diameter, and presenting a bevelled forward surface therebetween;
    inserting a cannula coaxially over said rod in order to further enlarge said passageway, said cannula presenting an inside diameter sufficient to allow insertion of surgical instruments therethrough and into said area; and
    removing said pin and said rod from said passageway subsequent to insertion of said cannula therein for allowing inserting of instruments through said cannula into said area.

11. The method set forth in claim 10, wherein said surgery is arthroscopic surgery performed on a joint area and said remote visualization device includes an arthroscope.

12. The method set forth in claim 10, wherein said surgery is endoscopic surgery performed on a body cavity and said remote visualization device includes an endoscope.

13. A method of performing surgery on an area surrounded by tissue, said method comprising the steps of:
    providing remote visualization of the area;
    creating a passageway between the area and the external surface of the surrounding tissue thereof by inserting a pin from said external surface through said surrounding tissue and thence into said area, such being the extent of the farthest penetration of said pin;
    remotely visualizing said pin in said area;
    enlarging said passageway by passing a tubular shaped rod coaxially over said pin and through said passageway while maintaining said pin in place and using said pin as a guide for said rod during insertion into said passageway,
    said rod presenting an inside diameter slightly greater than that of said pin;
    inserting a cannula coaxially over said rod in order to further enlarge said passageway,
    said cannula presenting an inside diameter slightly greater than the outside diameter of said rod,
    said inside diameter of said cannula being sufficient to allow insertion of surgical instruments therethrough and into said area; and
    removing said pin and said rod from said passageway subsequent to insertion of said cannula therein for inserting surgical instruments through said cannula into said area.

14. The method set forth in claim 13, wherein said surgery is arthroscopic surgery performed on a joint area.

15. The method set forth in claim 13, wherein said surgery is endoscopic surgery performed on a body cavity.

* * * * *